(12) United States Patent
Lin et al.

(10) Patent No.: US 11,375,613 B2
(45) Date of Patent: Jun. 28, 2022

(54) AEROSOL GENERATOR AND ATOMIZING MODULE

(71) Applicant: MICROBASE TECHNOLOGY CORP., Taoyuan (TW)

(72) Inventors: Chien-Hua Lin, Taoyuan (TW);
Shao-Yi Huang, Taoyuan (TW);
Yu-Chung Hsu, Taoyuan (TW);
Kai-Yao Lo, Taoyuan (TW)

(73) Assignee: MICROBASE TECHNOLOGY CORP., Taoyuan (TW)

( * ) Notice: Subject to any disclaimer, the term of this patent is extended or adjusted under 35 U.S.C. 154(b) by 776 days.

(21) Appl. No.: 16/353,770

(22) Filed: Mar. 14, 2019

(65) Prior Publication Data
US 2019/0335580 A1    Oct. 31, 2019

(30) Foreign Application Priority Data

Apr. 25, 2018  (CN) .......................... 201810381992.5

(51) Int. Cl.
*H05K 1/02*    (2006.01)
*H05K 1/11*    (2006.01)
(Continued)

(52) U.S. Cl.
CPC ......... *H05K 1/0278* (2013.01); *A61M 11/005* (2013.01); *B05B 17/0646* (2013.01);
(Continued)

(58) Field of Classification Search
CPC ...... H05K 1/0278; H05K 1/119; H05K 1/181; B05B 17/0646
See application file for complete search history.

(56) References Cited

U.S. PATENT DOCUMENTS 6,843,430 B2   1/2005   Boticki et al.
9,452,441 B2   9/2016   Hsieh et al.
(Continued)

FOREIGN PATENT DOCUMENTS

CN   103201047 A   7/2013
CN   203842759 U   9/2014
(Continued)

OTHER PUBLICATIONS

European Patent Office, European Search Report dated Sep. 23, 2019.
(Continued)

*Primary Examiner* — Jeremy C Norris
(74) *Attorney, Agent, or Firm* — Li & Cai Intellectual Property (USA) Office

(57) ABSTRACT

An aerosol generator includes a container and an atomizing module arranged in the container. The container has a liquid chamber and an aerosol chamber respectively arranged at two opposite sides of the atomizing module. The atomizing module includes an annular vibration plate, a microporous member, and a circuit board. The vibration plate has a first hole, and the microporous member is disposed on the vibration plate and covers the first hole. The circuit board is electrically coupled to an electrical contact of the vibration plate. The circuit board is arranged at one side of at least part of the vibration plate, and the circuit board and the at least part of the vibration plate have a gap there-between. A projected region defined by orthogonally projecting the circuit board onto a plane overlapping with the electrical contact partially covers the least part of the vibration plate.

20 Claims, 14 Drawing Sheets

(51) Int. Cl.
*A61M 11/00* (2006.01)
*B05B 17/00* (2006.01)
*H01R 12/71* (2011.01)
*H05K 5/00* (2006.01)
*H05K 1/18* (2006.01)

(52) U.S. Cl.
CPC ........... *H01R 12/714* (2013.01); *H05K 1/119* (2013.01); *H05K 5/006* (2013.01); *H05K 1/181* (2013.01); *H05K 2201/09027* (2013.01); *H05K 2201/09227* (2013.01); *H05K 2201/10083* (2013.01); *H05K 2201/10462* (2013.01)

(56) References Cited

U.S. PATENT DOCUMENTS

| | | |
|---|---|---|
| 2003/0218077 A1 | 11/2003 | Boticki et al. |
| 2008/0308096 A1 | 12/2008 | Borgschulte et al. |
| 2011/0265788 A1 | 11/2011 | Wu et al. |
| 2013/0113341 A1 | 5/2013 | Liu et al. |
| 2015/0375252 A1 | 12/2015 | Lee et al. |
| 2016/0167078 A1 | 6/2016 | Hogan et al. |

FOREIGN PATENT DOCUMENTS

| | | |
|---|---|---|
| CN | 204276252 U | 4/2015 |
| CN | 206183764 U | 5/2017 |
| CN | 107106790 A | 8/2017 |
| CN | 107626020 A | 1/2018 |
| CN | 208911162 U | 5/2019 |
| DE | 102005006374 B3 | 7/2006 |
| EP | 1604701 A1 | 12/2005 |
| EP | 2957349 A1 | 12/2015 |
| KR | 1020160146528 A | 12/2016 |
| TW | M338106 | 8/2008 |
| TW | I595930 B | 8/2017 |
| WO | 2011141475 A1 | 11/2011 |
| WO | 2012046220 A1 | 4/2012 |
| WO | WO 2015193432 A1 | 12/2015 |

OTHER PUBLICATIONS

European Patent Office, European Search Report dated Sep. 23, 2019 regarding EP patent application No. 19166513.2.

AEROSOL GENERATOR AND ATOMIZING MODULE

CROSS-REFERENCE TO RELATED PATENT APPLICATION

This application claims the benefit of priority to China Patent Application No. 201810381992.5, filed on Apr. 25, 2018 in People's Republic of China. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to an atomizing module, and more particularly to an aerosol generator and an atomizing module which are provided with a circuit board.

BACKGROUND OF THE DISCLOSURE

An atomizing module of conventional aerosol generator includes a vibration plate and a plurality of terminals arranged therein, and each of the terminals is directly abutted against the vibration plate so as to establish an electrical connection therebetween. That is to say, the conventional atomizing module does not have any buffering mechanism for the terminals. Accordingly, when the conventional atomizing module is in operation, the electrical connections between the vibration plate and each of the terminals tend to be unstable due to the vibration of the vibration plate.

SUMMARY OF THE DISCLOSURE

In response to the above-referenced technical inadequacies, the present disclosure provides an aerosol generator and an atomizing module which effectively improve the conventional atomizing modules.

In one aspect, the present disclosure provides an aerosol generator, which includes a container and an atomizing module. The container has a liquid chamber and an aerosol chamber. The atomizing module is assembled in the container. The liquid chamber and the aerosol chamber are respectively arranged at two opposite sides of the atomizing module. The atomizing module includes an annular vibration plate, a microporous member, and a circuit board. The vibration plate has a first hole and includes an electrical contact located on a plane. The microporous member is disposed on the vibration plate and covers the first hole. The liquid chamber and the aerosol chamber are in spatial communication with each other through the microporous member. The circuit board is electrically coupled to the electrical contact and is arranged at a side of at least part of the vibration plate. The circuit board and the at least part of the vibration plate have a gap therebetween. A projected region defined by orthogonally projecting the circuit board onto the plane partially covers the at least part of the vibration plate.

In certain embodiments, the atomizing module includes a solder fixed to the electrical contact and the circuit board so as to establish an electrical connection between the electrical contact and the circuit board.

In certain embodiments, the vibration plate is sequentially defined as an annular inner segment, an annular middle segment, and an annular outer segment along a direction away from the first hole; a width ratio of the inner segment, the middle segment, and the outer segment in a radius of the vibration plate is 1:3:3; and the electrical contact is arranged on at least one of the middle segment and the outer segment.

In certain embodiments, the circuit board includes an electrode region and a conductive circuit that is connected to the electrode region, and the electrode region is electrically coupled to the electrical contact through the conductive circuit and the solder.

In certain embodiments, the atomizing module includes a buffer sandwiched between the circuit board and a part of the vibration plate, and the gap is arranged between the circuit board and another part of the vibration plate and is in spatial communication with an external space.

In certain embodiments, the circuit board includes an electrode region electrically coupled to the electrical contact, and at least part of the buffer is arranged between the electrode region and the vibration plate.

In certain embodiments, the circuit board includes an external connecting arm arranged directly above at least one of the middle segment and the outer segment, and the solder connects the electrical contact and the external connecting arm.

In certain embodiments, the atomizing module includes a sheet-like carrier having a second hole, one of the microporous member, the vibration plate, and the carrier is sandwiched between the other two of the microporous member, the vibration plate, and the carrier, and wherein the microporous member covers the second hole, and the liquid chamber and the aerosol chamber are in spatial communication with each other through a portion of the microporous member that covers the second hole.

In certain embodiments, the circuit board has a positioning portion fastened to the container so as to hang the circuit board over the at least part of the vibration plate.

In certain embodiments, the vibration plate further includes another electrical contact, and the two electrical contacts of the vibration plate are arranged on the same surface of the vibration plate.

In one aspect, the present disclosure provides an atomizing module, which includes an annular vibration plate, a microporous member, and a circuit board. The vibration plate has a first hole and includes an electrical contact located on a plane. The microporous member is disposed on the vibration plate and covers the first hole. The circuit board is electrically coupled to the electrical contact and arranged at a side of at least part of the vibration plate. The circuit board and the at least part of the vibration plate have a gap therebetween, and a projected region defined by orthogonally projecting the circuit board onto the plane partially covers the at least part of the vibration plate.

In certain embodiments, the atomizing module further includes a buffer, the buffer is sandwiched between the circuit board and a part of the vibration plate, and the gap is arranged between the circuit board and another part of the vibration plate and is in spatial communication with an external space.

In certain embodiments, the circuit board includes an electrode region electrically coupled to the electrical contact, and at least part of the buffer is arranged between the electrode region and the vibration plate.

In certain embodiments, the circuit board includes an electrode region electrically coupled to the electrical contact, and a portion of the projected region with respect to the electrode region is located outside of the electrical contact.

In certain embodiments, the atomizing module further includes a solder, and the solder is fixed to the electrical contact and the circuit board so as to establish an electrical connection between the electrical contact and the circuit board.

In certain embodiments, the vibration plate is sequentially defined as an annular inner segment, an annular middle segment, and an annular outer segment along a direction away from the first hole; a width ratio of the inner segment, the middle segment, and the outer segment in to a radius of the vibration plate is 1:3:3; and the electrical contact is arranged on at least one of the middle segment and the outer segment.

In certain embodiments, the circuit board includes an electrode region and a conductive circuit that is connected to the electrode region, and the electrode region is electrically coupled to the electrical contact through the conductive circuit and the solder.

In certain embodiments, the circuit board includes an external connecting arm arranged directly above at least one of the middle segment and the outer segment, and the solder connects the electrical contact and the external connecting arm.

In certain embodiments, the atomizing module further includes a sheet-like carrier having a second hole, and one of the microporous member, the vibration plate, and the carrier is sandwiched between the other two of the microporous member, the vibration plate, and the carrier, and wherein the microporous member covers the second hole.

In certain embodiments, the vibration plate further includes another electrical contact, and the two electrical contacts of the vibration plate are arranged on the same surface of the vibration plate.

Therefore, in the aerosol generator and the atomizing module of the present disclosure, the circuit board is spaced apart from and is electrically coupled to the vibration plate, so that the conductive terminal needs to abut against the circuit board to be electrically coupled to the vibration plate. Accordingly, the electrical connection between the circuit board and the conductive terminal is not easily affected by the vibration generated from the vibration plate, thereby being more stable.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
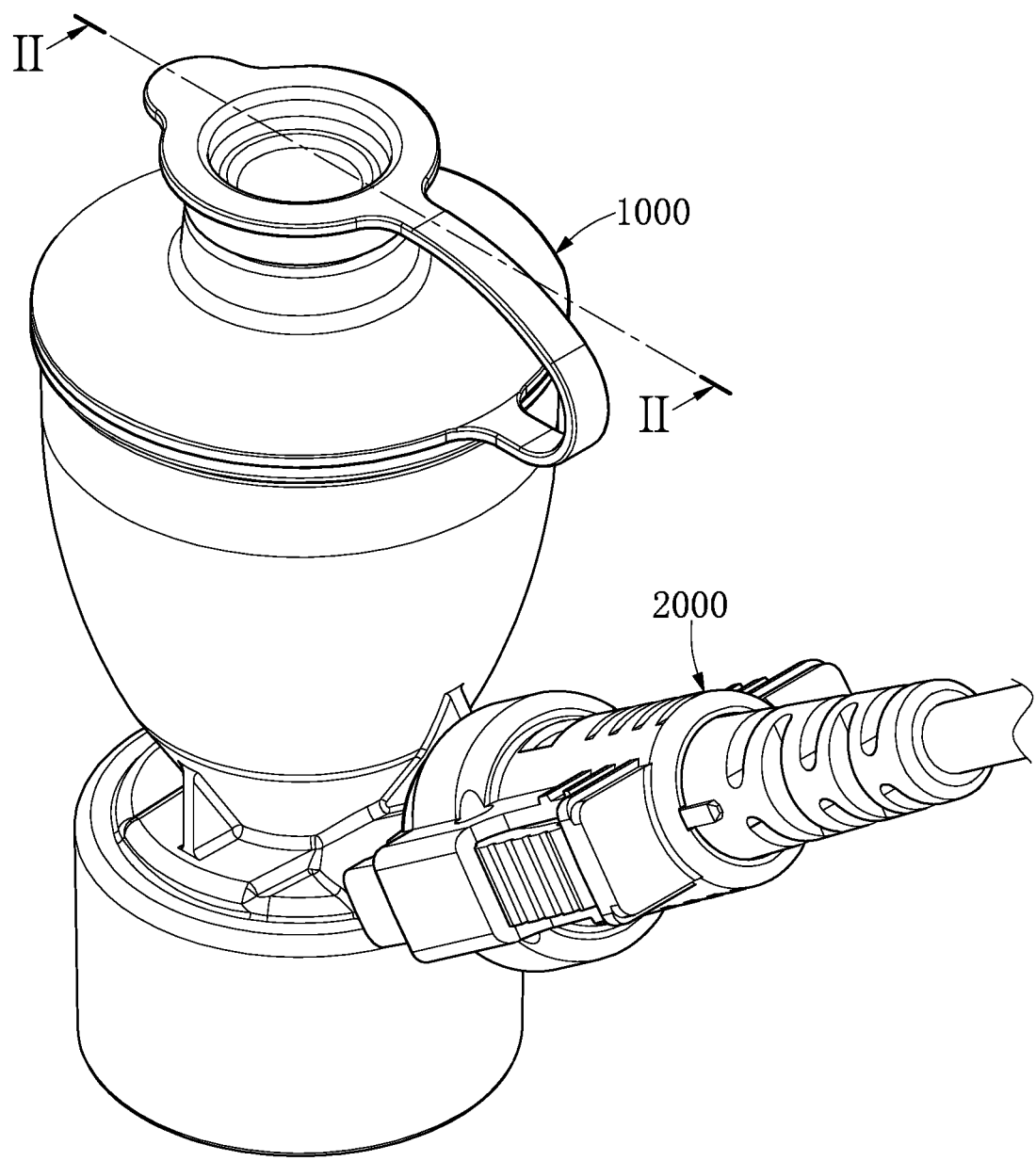
FIG. 1 is a perspective view of an aerosol generating device according the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
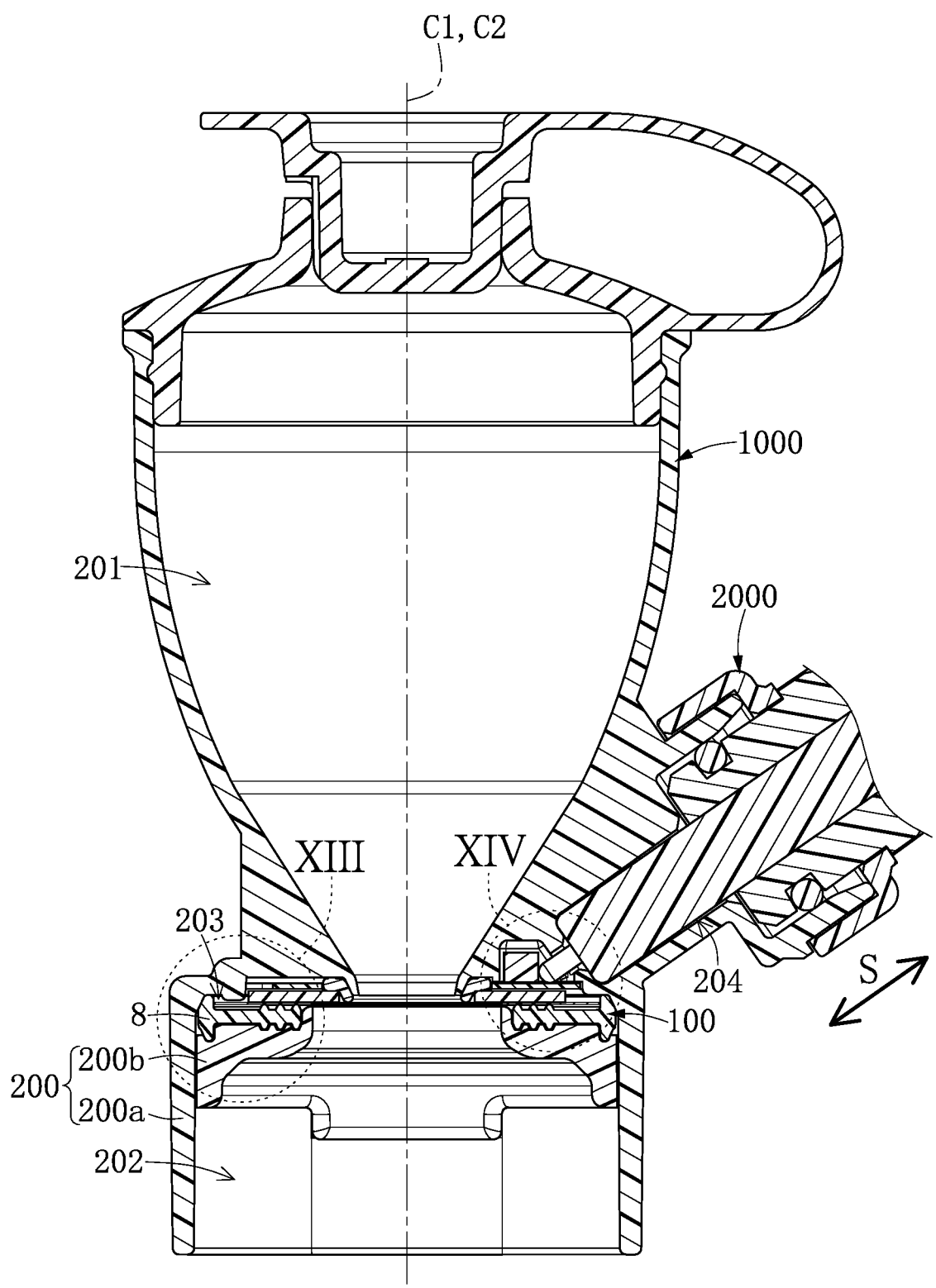
FIG. 2 is a cross-sectional view taken along line II-II of FIG. 1.
Figure 3:
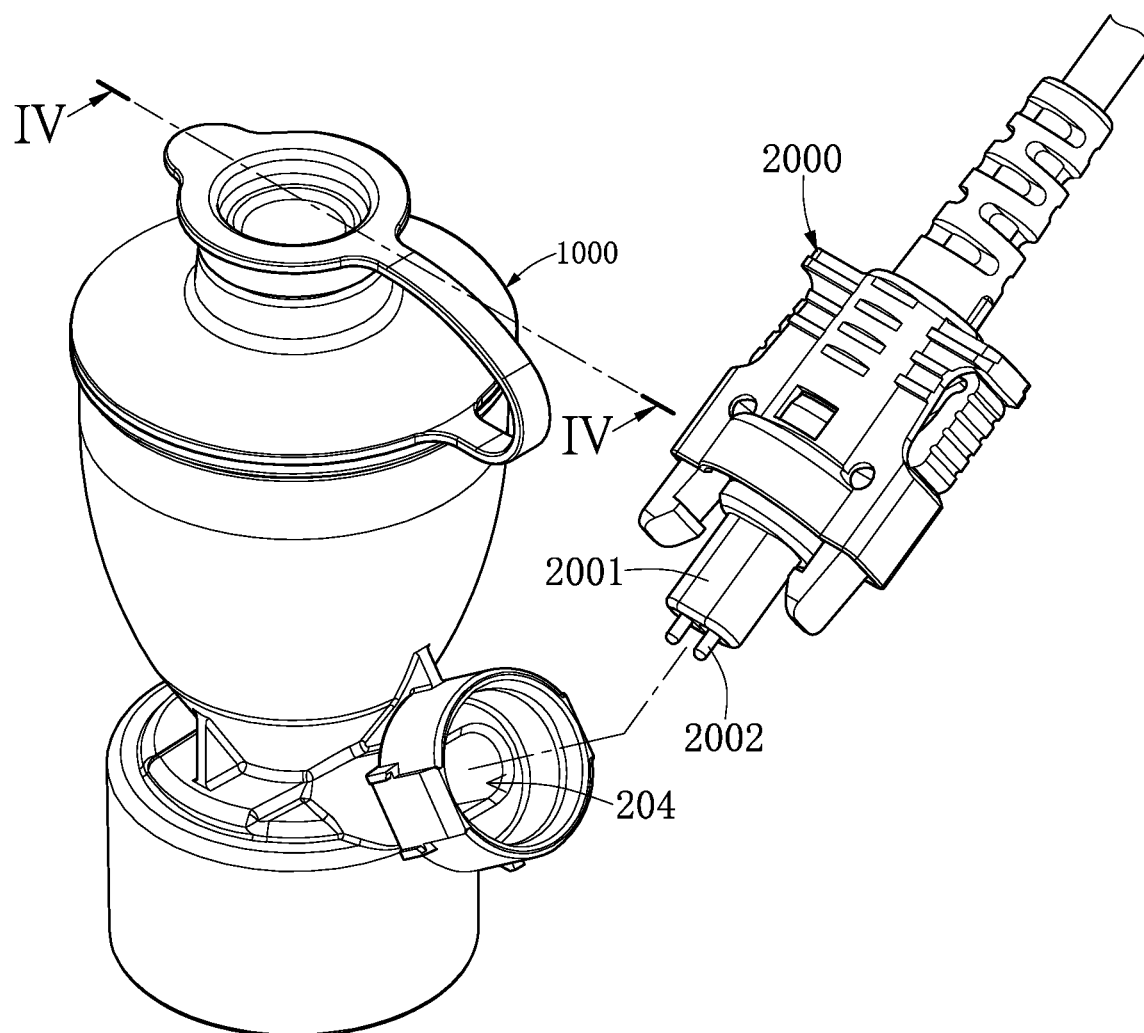
FIG. 3 is an exploded view of FIG. 1.

Referring to FIG. 1 to FIG. 15, an embodiment of the present disclosure provides an aerosol generating device that can be applied to the medical field, but the present disclosure is not limited thereto. As shown in FIG. 1 to FIG. 3, the aerosol generating device includes an aerosol generator 1000 and a plug 2000 detachably inserted into the aerosol generator 1000. The plug 2000 is electrically coupled to an external electricity source (not shown) for driving the aerosol generator 1000. It should be noted that, the aerosol generator 1000 in the present embodiment is cooperated with the plug 2000, but in other embodiments of the present disclosure, the aerosol generator 1000 can be independently applied or can be cooperated with other components.

Figure 4:
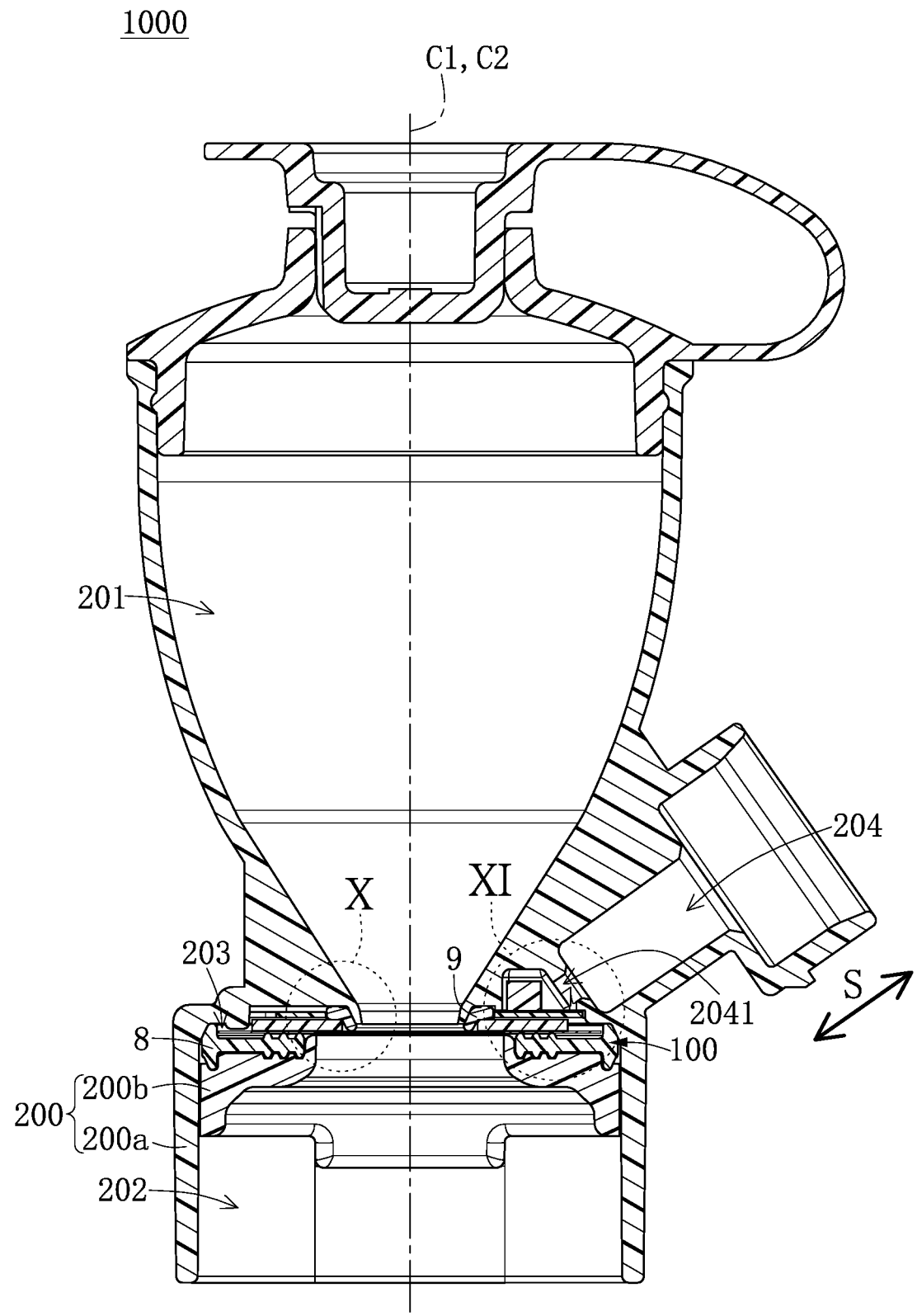
FIG. 4 is a cross-sectional view taken along line IV-IV of FIG. 3.
Figure 5:
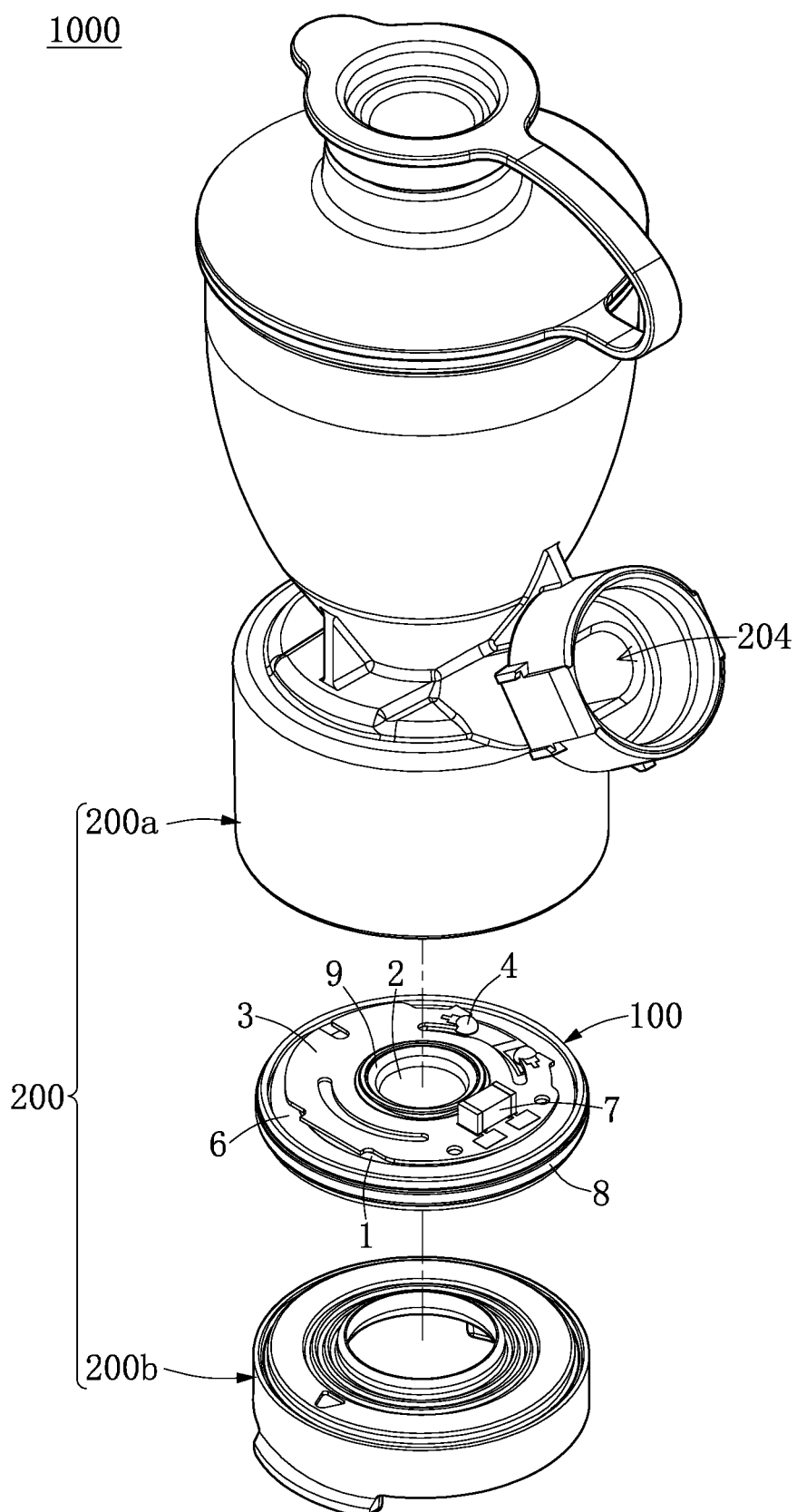
FIG. 5 is an exploded view of an aerosol generator according to the present disclosure.

As shown in FIG. 4 and FIG. 5, the aerosol generator 1000 includes a container 200 and an atomizing module 100 assembled in the container 200. It should be noted that, the atomizing module 100 in the present embodiment is cooperated with the container 200, but in other embodiments of the present disclosure, the atomizing module 100 can be independently applied or can be cooperated with other components.

Moreover, the container 200 has a liquid chamber 201, an aerosol chamber 202, a receiving chamber 203 arranged between the liquid chamber 201 and the aerosol chamber 202, and an insertion slot 204 that is in spatial communication with the receiving chamber 203. In other words, the container 200 of the present embodiment is formed by a cup 200a and a cover 200b assembled in (e.g., screwed into) the cup 200a, and the atomizing module 100 is sandwiched between the cup 200a and the cover 200b, but the present disclosure is not limited thereto. In the present embodiment, the cup 200a defines the liquid chamber 201 and the insertion slot 204, and the cup 200a and the cover 200b jointly define the aerosol chamber 202 and the receiving chamber 203.

The atomizing module 100 is disposed in the receiving chamber 203 of the container 200. That is to say, the liquid chamber 201 and the aerosol chamber 202 are respectively arranged at two opposite sides of the atomizing module 100 (e.g., the upper side and the lower side of the atomizing module 100 shown in FIG. 4), and are in spatial communication with each other through the atomizing module 100. The insertion slot 204 is configured to receive and hold the plug 2000, and the plug 2000 is electrically coupled to the atomizing module 100 so as to provide electric power to drive the atomizing module 100.

Specifically, the liquid chamber 201 is configured to receive medicinal liquid (not shown), and when the medicinal liquid flows from the liquid chamber 201 toward the aerosol chamber 202, the medicinal liquid is atomized to become atomized liquid by the atomizing module 100, so that a user can inhale the atomized liquid from the aerosol chamber 202. The atomized liquid in the present embodiment means particles of the atomized liquid each having a diameter within a range of 3.5~3.5 μm. The container 200 can be adjusted or changed according to design requirements.

In the present embodiment, a central axis C1 of the liquid chamber 201 overlaps a central axis C2 of the aerosol chamber 202. The liquid chamber 201 is tapered along a direction toward the aerosol chamber 202, and the liquid chamber 201 in the present embodiment is approximately in a warhead shape. Accordingly, the structure of the liquid chamber 201 can provide the medicinal liquid to flow smoothly, thereby effectively preventing bubbles from being generated in the medicinal liquid.

Moreover, the insertion slot 204 of the present embodiment defines an insertion direction S. In other words, the plug 2000 is inserted into the insertion slot 204 along the insertion direction S. The insertion direction S and the central axis C1 of the liquid chamber 201 have an acute angle therebetween. The insertion slot 204 has a thru-hole 2041 that is in spatial communication with the receiving chamber 203. The insertion slot 204 in the present embodiment is not integrally formed with any conductive terminal, or is not undetachably fixed with any conductive terminal. Accordingly, when the container 200 is abandoned after being used, the abandoned container 200 does not have any conductive terminal, thereby effectively avoiding waste of resources, but the present disclosure is not limited thereto. For example, in other embodiments of the present disclosure, the insertion slot 204 can be undetachably fixed with at least one conductive terminal.

Figure 6:
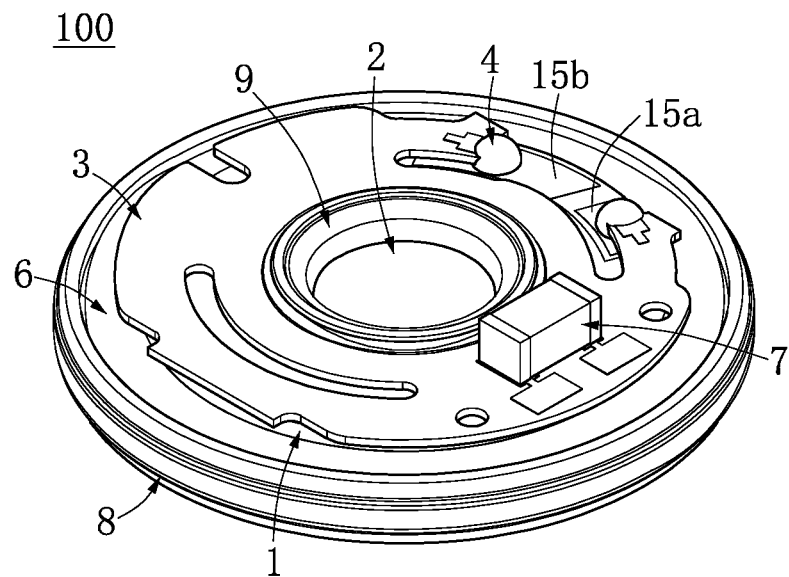
FIG. 6 is a perspective view of an atomizing module according to the present disclosure.
Figure 7:
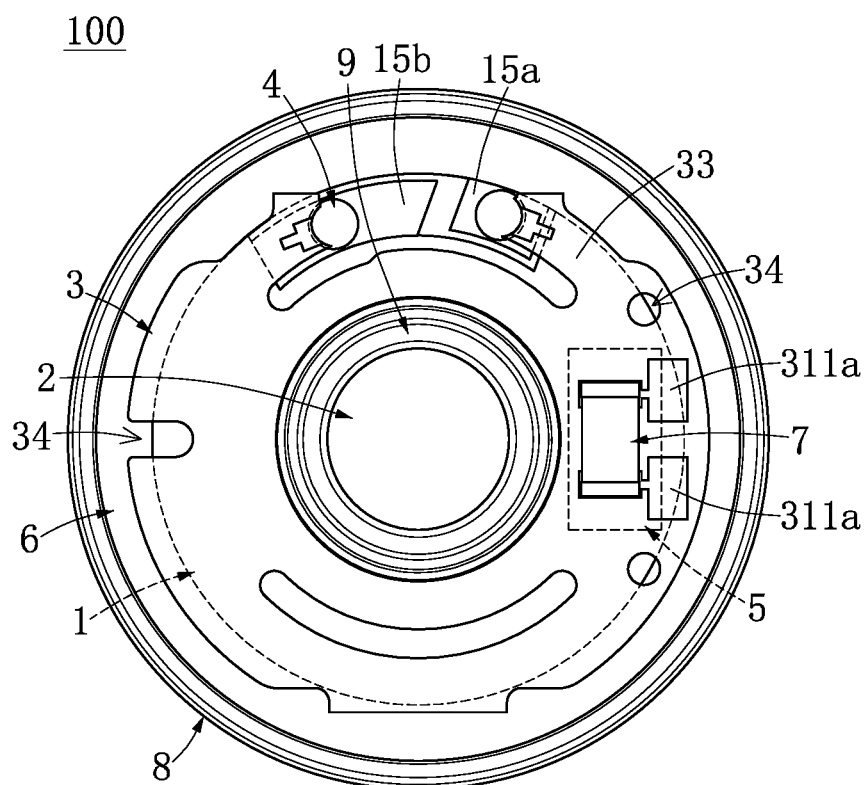
FIG. 7 is a top view of FIG. 6.
Figure 8:
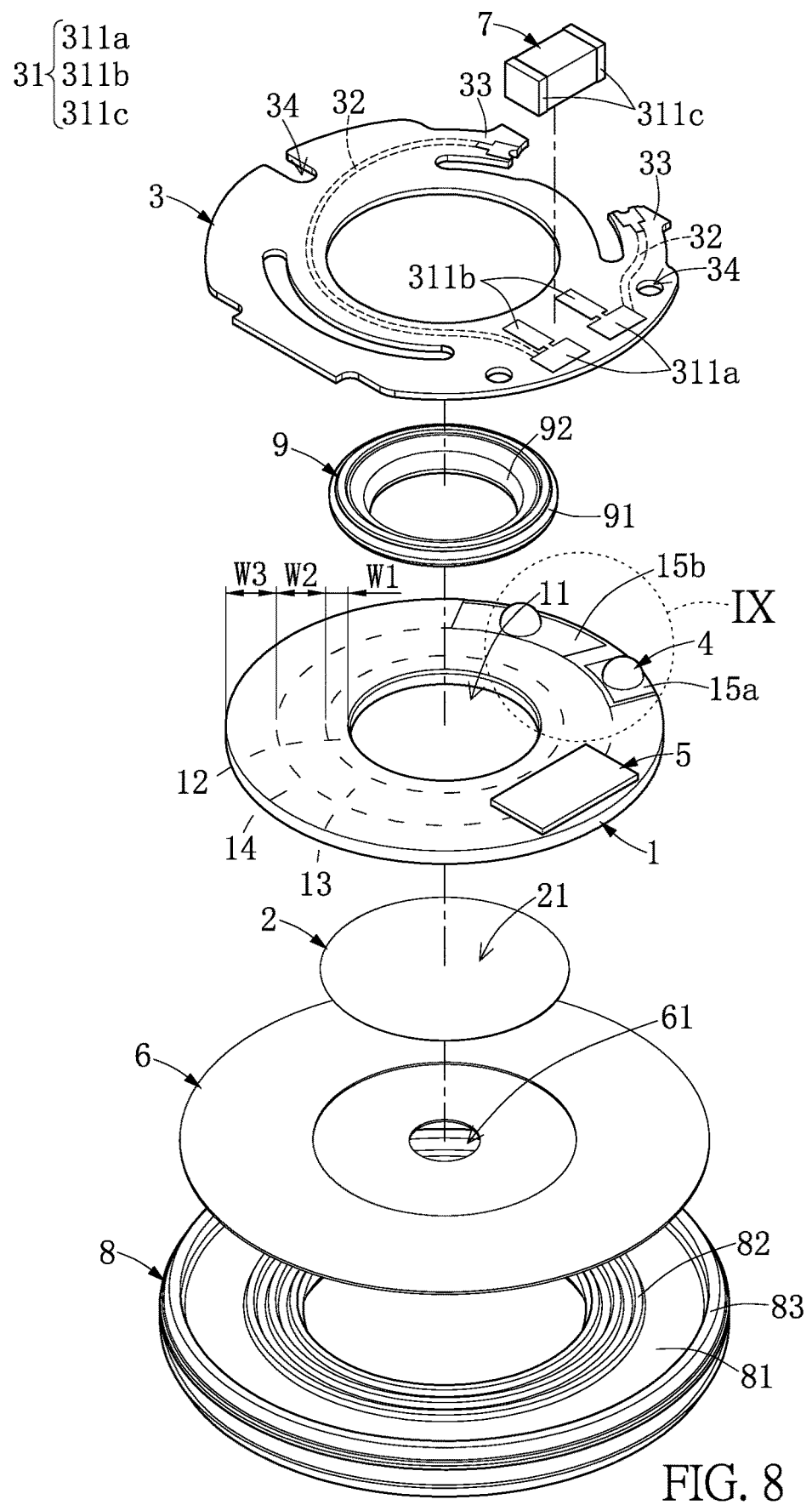
FIG. 8 is an exploded view of FIG. 6.

As shown in FIG. 6 to FIG. 8, the atomizing module 100 in the present embodiment includes an annular vibration plate 1, a microporous member 2 disposed on the vibration plate 1, a circuit board 3 electrically coupled to the vibration plate 1, two solders 4 electrically connected to the vibration plate 1 and the circuit board 3, a buffer 5 sandwiched between the vibration plate 1 and the circuit board 3, a sheet-like carrier 6 carrying the vibration plate 1, an electronic component 7 mounted on the circuit board 3, a bottom gasket 8 sandwiched between the carrier 6 and the container 200 (e.g., the cover 200b shown in FIG. 4), and an inner gasket 9 sandwiched between the vibration plate 1 and the container 200 (e.g., the cup 200a shown in FIG. 4).

It should be noted that, while the atomizing module 100 in the present embodiment includes the above components, the present disclosure is not limited thereto. For example, in other embodiments of the present disclosure, the number, structure, or connection relationship of each component of the atomizing module 100 can be adjusted according to design requirements, and the atomizing module 100 can be cooperated with components other than the above components of the present embodiment.

As shown in FIG. 7 and FIG. 8, the vibration plate 1 in the present embodiment is a ring-shaped piezoelectric (PZT) plate, and has a circular first hole 11 defined by an inner edge thereof. The vibration plate 1 is sequentially defined as an annular inner segment 12, an annular middle segment 13, and an annular outer segment 14 along a direction away from the first hole 11. Specifically, a width ratio (i.e., W1:W2:W3) of the inner segment 12, the middle segment 13, and the outer segment 14 in a radius of the vibration plate 1 is 1:3:3, but the present disclosure is not limited thereto.

Moreover, the vibration plate 1 includes two electrical contacts 15a, 15b arranged on the same surface thereof (e.g., the top surface of the vibration plate 1 shown in FIG. 8) or located on a first plane. Since the two electrical contacts 15a, 15b cannot be vibrated, each of the two electrical contacts 15a, 15b is preferably arranged on at least one of the middle segment 13 and the outer segment 14 of the vibration plate 1 so as to avoid affecting the vibration performance of the vibration plate 1. The number of the electrical contacts 15a, 15b of the vibration plate 1 in the present embodiment is two, but in other embodiments of the present disclosure, the vibration plate 1 can include only one electrical contact.

Figure 9:
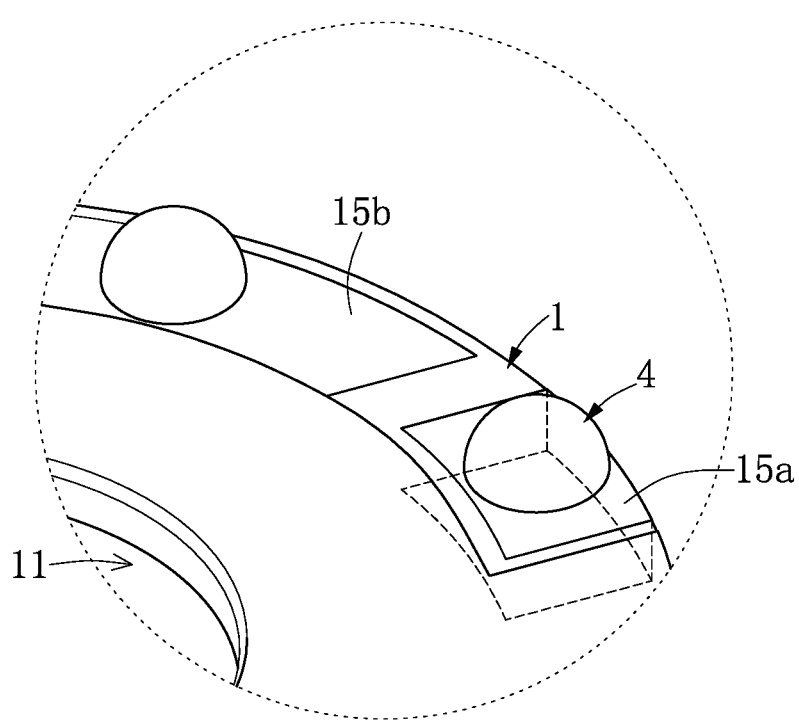
FIG. 9 is an enlarged view of portion IX of FIG. 8.

In addition, the structure of each of the two electrical contacts 15a, 15b can be adjusted according to design requirements. In the present embodiment, as shown in FIG. 9, the vibration plate 1 includes a top electrode and a bottom electrode both respectively arranged on a top surface and a bottom surface of a periphery portion thereof, and the top electrode is defined as the electrical contact 15b. Moreover, the bottom electrode (e.g., a substantially rectangular portion of the vibration plate 1 presented by the dotted lines shown in FIG. 9) is further formed with a conductive layer that extends from the bottom electrode to the top surface of the periphery portion of the vibration plate 1 through a lateral side of the vibration plate 1, and a portion of the conductive layer arranged on the top surface of the vibration plate 1 is defined as the electrical contact 15a.

Figure 10:
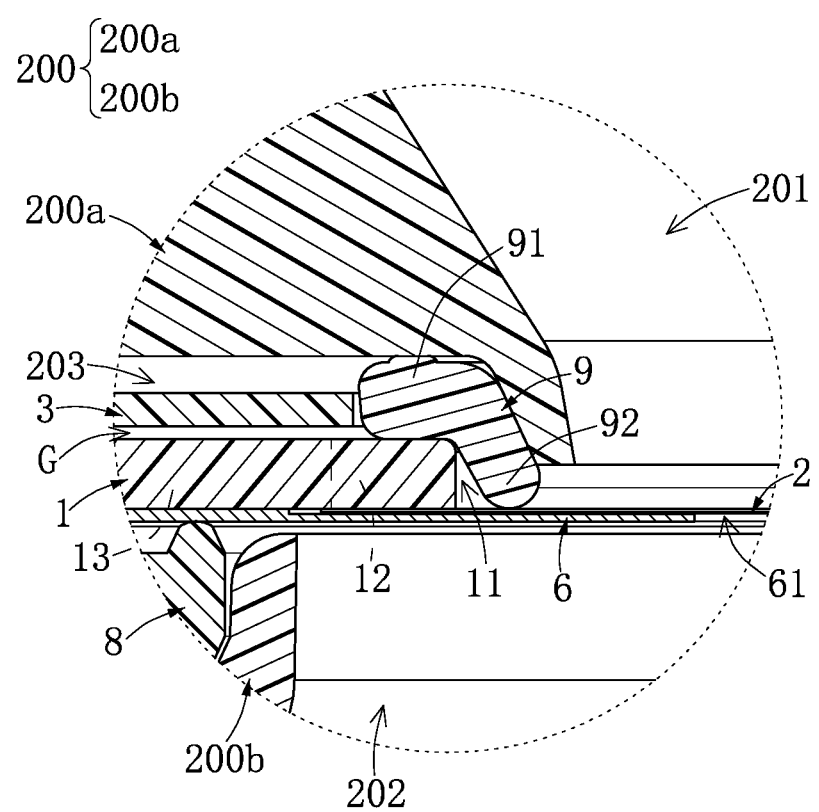
FIG. 10 is an enlarged view of portion X of FIG. 4.

As shown in FIG. 8 and FIG. 10, the microporous member 2 in the present embodiment is a circular film made of a metallic material or a polymeric material, and the microporous member 2 has a plurality of atomizing holes 21 penetratingly formed in a substantially central portion thereof. The number and structure of the atomizing holes 21 can be adjusted according to design requirements (e.g., the diameter of particles of the atomized liquid).

Moreover, the microporous member 2 is disposed on the vibration plate 1 and covers the first hole 11, and the microporous member 2 in the present embodiment is sandwiched between the vibration plate 1 and the carrier 6, but the present disclosure is not limited thereto. For example, in other embodiments of the present disclosure, one of the microporous member 2, the vibration plate 1, and the carrier 6 can be sandwiched between the other two of the microporous member 2, the vibration plate 1, and the carrier 6. Accordingly, the liquid chamber 201 and the aerosol chamber 202 of the container 200 are in spatial communication with each other through the microporous member 2.

Specifically, the carrier 6 in the present embodiment is in an annular shape and has a circular second hole 61 defined by an inner edge thereof, and a diameter of the second hole 61 is smaller than that of the first hole 11. The microporous member 2 covers the second hole 61 of the carrier 6 (i.e., the first hole 11 and the second hole 61 are separate from each other by the microporous member 2), so that the liquid chamber 201 and the aerosol chamber 202 are in spatial communication with each other through a portion of the microporous member 2 that covers the second hole 61. Moreover, the atomizing holes 21 of the microporous member 2 are preferably arranged in the portion of the microporous member 2 that covers the second hole 61.

Figure 11:
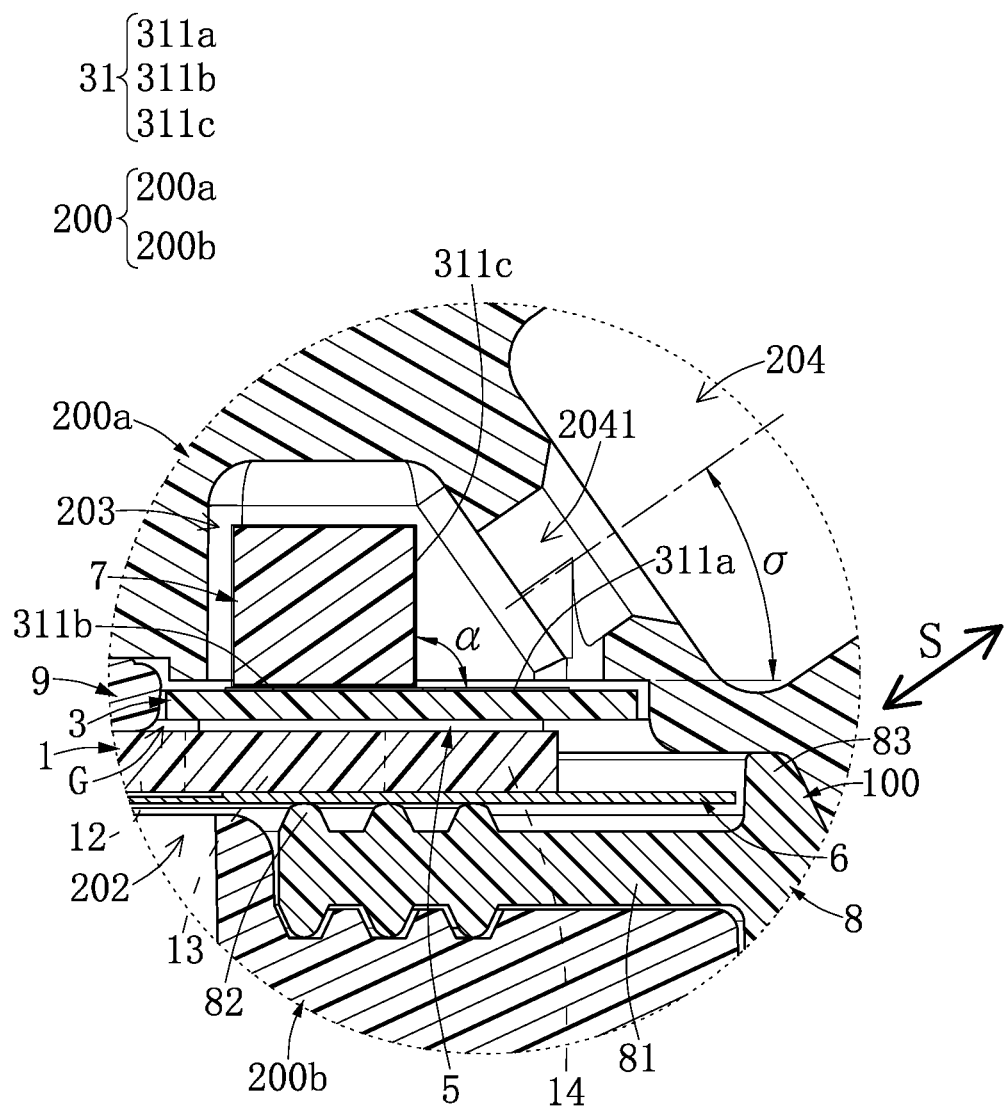
FIG. 11 is an enlarged view of portion XI of FIG. 4.

As shown in FIG. 7, FIG. 8, and FIG. 11, the circuit board 3 is arranged at a side of at least part of the vibration plate 1, and the circuit board 3 and the at least part of the vibration plate 1 have a gap G therebetween. Moreover, a first projected region defined by orthogonally projecting the circuit board 3 onto the first plane (e.g., the top surface of the vibration plate 1 shown in FIG. 11) partially covers the at least part of the vibration plate 1. In other words, the circuit board 3 is approximately spaced apart from (or located at) one side of the vibration plate 1 (e.g., the upper side of the vibration plate 1 shown in FIG. 11) away from the carrier 6 or the aerosol chamber 202. That is to say, the circuit board 3 in the present embodiment is arranged directly above the vibration plate 1.

Specifically, the circuit board 3 and the vibration plate 1 in the present embodiment can be spaced apart from each other by at least one of the buffer 5 and the solders 4, and the detail features are disclosed in the following description. In addition, since the circuit board 3 has a positioning portion 34 fastened to the container 200, the circuit board 3 can be spaced apart from the side of the at least part of the vibration plate 1 by the cooperation of the container 200 and the positioning portion 34, but the present disclosure is not limited thereto.

For example, in other embodiments of the present disclosure, the circuit board 3 and the vibration plate 1 can be provided without any structural support or connection therebetween. In other words, the circuit board 3 can be hung over the at least part of the vibration plate 1 only by the cooperation of the container 200 and the positioning portion 34.

Figure 12:
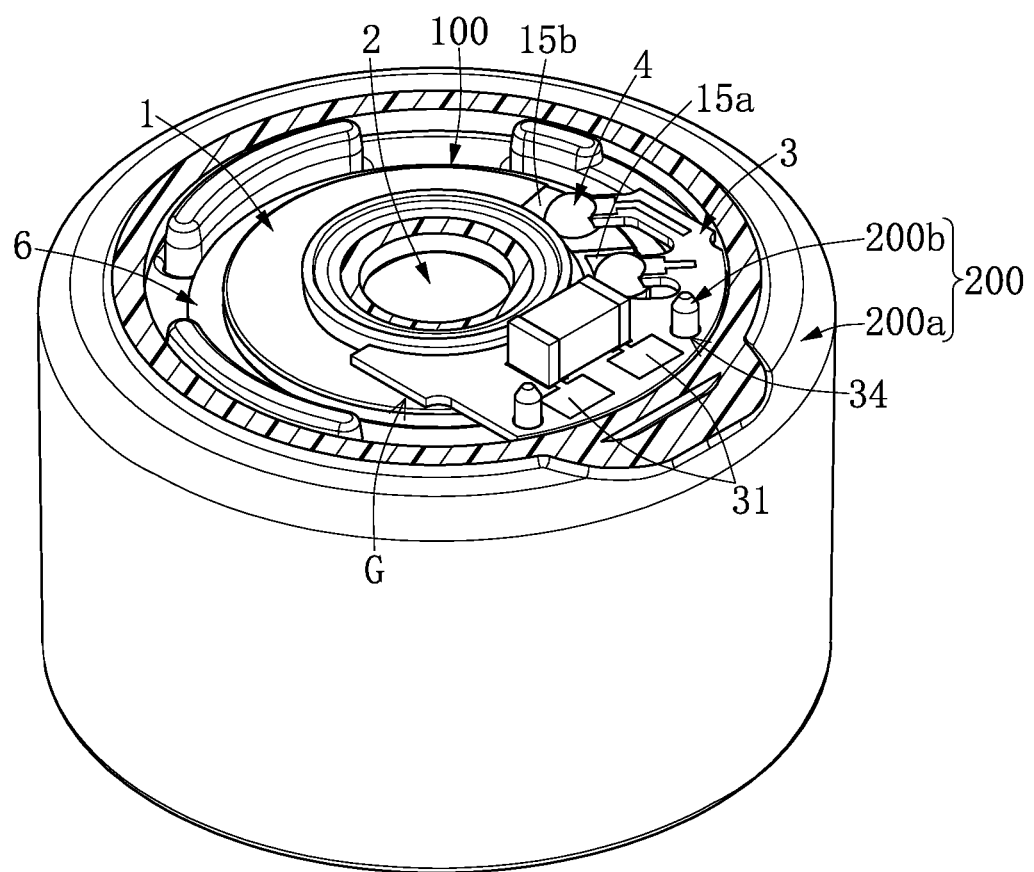
FIG. 12 is a cross-sectional view of the aerosol generator in another configuration according to the present disclosure.

The circuit board 3 in the present embodiment is in a substantially annular shape, but the shape and size of the circuit board 3 can be adjusted according to design requirements. For example, the circuit board 3 can be a structure as shown in FIG. 12.

As shown in FIG. 7, FIG. 8, and FIG. 11, the circuit board 3 is electrically coupled to the two electrical contacts 15a, 15b of the vibration plate 1. In the present embodiment, the circuit board 3 is electrically coupled to the two electrical contacts 15a, 15b by the solders 4 (e.g., two solder balls), and the solders 4 are fixed to the electrical contacts 15a, 15b and the circuit board 3 so as to establish an electrical connection between the electrical contacts 15a, 15b and the circuit board 3, but the present disclosure is not limited thereto. In other embodiments of the present disclosure, the circuit board 3 can be electrically coupled to the two electrical contacts 15a, 15b by cables.

The circuit board 3 includes two adjacent conductive portions 31 spaced apart from each other and two conductive circuits 32 respectively connected to the two conductive portions 31. The two conductive portions 31 have different polarities, and each of the two conductive portions 31 has two electrode regions 311a, 311b. The two electrode regions 311a, 311b of one of the two conductive portions 31 are respectively arranged adjacent to the two electrode regions 311a, 311b of the other conductive portion 31. The two conductive portions 31 are respectively and electrically coupled to the two electrical contacts 15a, 15b through the conductive circuits 32 and the solders 4. The two conductive circuits 32 in the present embodiment preferably have different lengths.

Moreover, the number of the conductive portions 31 (or the electrode regions 311a, 311b) and the number of the conductive circuits 32 of the circuit board 3 can be adjusted according to design requirements. For example, in other embodiments of the present disclosure, the circuit board 3 can include only one conductive portion 31 and only one conductive circuit 32 connected to the conductive portion 31; or the circuit board 3 can include only one of the electrode regions 311a, 311b and only one conductive circuit 32 connected to the electrode region 311a, 311b; or the circuit board 3 can include only one electrode region 311a, 311b, and the electrode region 311a, 311b is directly connected to the corresponding electrical contact 15a, 15b or is electrically coupled to the corresponding electrical contact 15a, 15b by a cable.

Specifically, as shown in FIG. 7, FIG. 8, and FIG. 11, each of the electrode regions 311a, 311b is arranged on a surface of the circuit board 3 (e.g., the top surface of the circuit board 3 shown in FIG. 8) away from the vibration plate 1. Portions of the first projected region with respect to the electrode regions 311a, 311b are located outside of the electrical contacts 15a, 15b. That is to say, the portions of the first projected region defined by orthogonally projecting the electrode regions 311a, 311b onto the first plane (e.g., the top surface of the vibration plate 1 shown in FIG. 7) are located outside of the electrical contacts 15a, 15b. In other words, as shown in FIG. 11, at least part of each of the electrode regions 311a, 311b is substantially arranged above a portion of at least one of the middle segment 13 and the outer segment 14 of the vibration plate 1 that is not formed with the electrical contacts 15a, 15b.

The circuit board 3 includes two external connecting arms 33 hung over and arranged directly above at least one of the middle segment 13 and the outer segment 14 of the vibration plate 1. Free ends of the two external connecting arms 33 in the present embodiment are arranged approximately above the two electrical contacts 15a, 15b of the vibration plate 1, respectively, so that the free end of each of the two external connecting arms 33 can swing slightly and elastically. In addition, in other embodiments of the present disclosure, the circuit board 3 can be formed with only one external connecting arm 33 or no external connecting arm 33.

Moreover, each of the two conductive circuits 32 has a first end and an opposite second end. The first ends of the two conductive circuits 32 are respectively connected to the two conductive portions 31 of the circuit board 3, and the second ends of the two conductive circuits 32 are respectively arranged on the free ends of the two external connecting arms 33. The two solders 4 connected to the two electrical contacts 15a, 15b are respectively soldered to the two external connecting arms 33, thereby electrically connecting to the conductive circuits 32 on the external connecting arms 33. The circuit board 3 can absorb any deviation generated from a soldering process of the solders 4 by the swingability of each of the external connecting arms 33, thereby effectively preventing empty soldering issues from occurring As shown in FIG. 8 and FIG. 11, the two electrode regions 311a, 311b of each of the conductive portions 31 are located on a second plane (e.g., the top surface of the circuit board 3 shown in FIG. 11), and the central axis C2 of the aerosol chamber 202 is substantially perpendicular to the second plane (as shown in FIG. 2 and FIG. 11). Moreover, each of the conductive portions 31 in the present embodiment further includes another electrode region 311c. In the two electrode regions 311a, 311c of each of the conductive portions 31, one of the two electrode regions 311a, 311c (i.e., the electrode region 311a) is located on the second plane (e.g., the top surface of the circuit board 3 shown in FIG. 11) substantially perpendicular to the central axis C2, and the other electrode region 311c is located on a third plane other than the first and second planes. The two electrode regions 311a, 311c have an angle therebetween that is within a range of 70~110 degrees.

It should be noted that, the arrangement of the electrode region 311c can be adjusted according to design requirements. In the present embodiment, the electrode region 311c of each of the conductive portions 31 is disposed on/around an outer surface of the electronic component 7. Specifically, the electronic component 7 is disposed on the surface (e.g., the top surface) of the circuit board 3 away from the vibration plate 1, and spans across the electrode regions 311b of the two conductive portions 31, so that the two electrode regions 311c on the electronic component 7 are respectively connected to the two electrode regions 311b on the top surface of the circuit board 3 for establishing electrical connection therebetween. Accordingly, the electrode regions 311a of the two conductive portions 31 which are not covered by the electronic component 7 are arranged on the top surface of the circuit board 3 (or are located on the second plane), and the two electrode regions 311a, 311c of each of the two conductive portions 31 have an angle α therebetween that is within a range of 70~110 degrees. The angle α in the present embodiment is 90 degrees, but the present disclosure is not limited thereto.

The electrode regions 311a, 311b, 311c in the present embodiment are formed on the circuit board 3 and the electronic component 7, but the position and number of the electrode regions 311a, 311b, 311c can be adjusted according to design requirements. For example, in other embodiments of the present disclosure, the atomizing module 100 can exclude the electronic component 7 and the electrode regions 311c, so that all of the electrode regions 311a, 311b of the conductive portions 31 are located on the same plane (e.g., the second plane); or each of the conductive portions 31 of the atomizing module 100 can include only two electrode regions 311a, 311c that are located on different planes (e.g., the second plane and the third plane); or the atomizing module 100 can exclude the circuit board 3, and the electrical contacts 15a, 15b of the vibration plate 1 are used as electrode regions.

As shown in FIG. 11, the top surface of the circuit board 3 (e.g., the second plane) and the insertion direction S of the insertion slot 204 of the container 200 have an acute angle σ therebetween that is within a range of 30~60 degrees. Moreover, a second projected region defined by projecting an inner wall defining the thru-hole 2041 onto the atomizing module 100 along the insertion direction S is located on the two electrode regions 311a, 311c of each of the conductive portions 31.

However, an angle between the top surface of the circuit board 3 and the insertion direction S of the insertion slot 204 in the present embodiment is within a range of 30~60 degrees, but the present disclosure is not limited thereto. In other embodiments of the present disclosure, an angle between the top surface of the circuit board 3 and the insertion direction S of the insertion slot 204 can be other values (e.g., 90 degrees).

As shown in FIG. 7, FIG. 8, and FIG. 11, the buffer 5 in the present embodiment is a solidified adhesive, but the present disclosure is not limited thereto. For example, in other embodiments of the present disclosure, the buffer 5 can be a sponge, a spring, or other members having buffering effects.

The buffer 5 is sandwiched between the circuit board 3 and a part of the vibration plate 1, and the gap G is arranged between the circuit board 3 and another part of the vibration plate 1 and is in spatial communication with an external space. In the present embodiment, the buffer 5 has two opposite ends, one of the two ends of the buffer 5 connects with the circuit board 3, and the other end of the buffer 5 connects with at least one of the middle segment 13 and the outer segment 14 of the vibration plate 1. In other words, the gap G is in an annular shape and is arranged between the circuit board 3 and the inner segment 12 of the vibration plate 1, and the buffer 5 is arranged outside of the gap G.

Specifically, at least part of the buffer 5 is arranged under the two electrode regions 311a, 311c of each of the conductive portions 31 (i.e., the at least part of the buffer 5 is arranged between the vibration plate 1 and the electrode regions 311a, 311c), so that the buffer 5 can provide a buffering effect between the vibration plate 1 and a portion of the circuit board 3 having the electrode regions 311a, 311c. Accordingly, the electrode regions 311a, 311c of the circuit board 3 can receive a larger pressing force. Moreover, the middle segment 13 and the outer segment 14 each have a surface facing the vibration plate 1, and 3~30% of the surfaces of the middle segment 13 and the outer segment 14 are connected to the buffer 5.

In other embodiments of the present disclosure, space between the circuit board 3 and the vibration plate 1 can be provided without the buffer 5, can be provided with a plurality of buffers 5, or can be fully filled with the buffer 5 according to design requirements.

Figure 13:
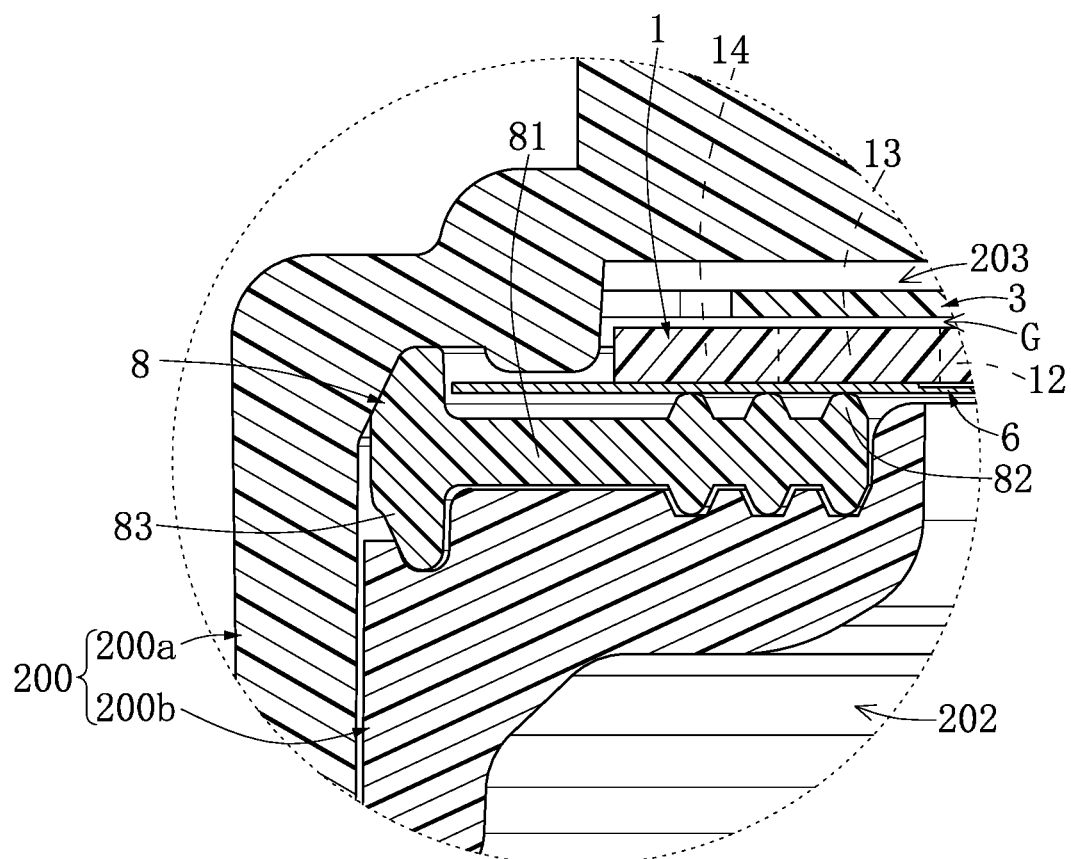
FIG. 13 is an enlarged view of portion XIII of FIG. 2.

As shown in FIG. 8 and FIG. 13, the bottom gasket 8 in the present embodiment is an annular structure (e.g., an annular rubber) with resilient property. The bottom gasket 8 has a hole defined by an inner edge thereof, and a diameter of the hole of the bottom gasket 8 is larger than that of the first hole 11 of the vibration plate 1. The bottom gasket 8 includes an annular sheet 81, a plurality of annular ribs 82 respectively extending from two opposite surfaces of the annular sheet 81, and an annular flange 83 extending from an outer lateral edge of the annular sheet 81.

In a top view of the bottom gasket 8, the annular ribs 82 and the annular flange 83 are concentric circles, and any two of the annular ribs 82 adjacent to each other have the same gap. A height of each of the annular ribs 82 with respect to the annular sheet 81 is smaller than a height of the annular flange 83 with respect to the annular sheet 81, but the present disclosure is not limited thereto.

Moreover, the bottom gasket 8 is disposed on the cover 200b of the container 200, the annular ribs 82 are sandwiched between the carrier 6 and the cover 200b of the container 200 (i.e., the carrier 6 is disposed on the annular ribs 82), the annular flange 83 is sandwiched between and gaplessly connected to the cup 200a and the cover 200b of the container 200, and a center of the bottom gasket 8 is substantially located on the central axis C2 of the aerosol chamber 202 (as shown in FIG. 2).

Specifically, as shown in FIG. 11, a third projected region defined by orthogonally projecting the annular ribs 82 onto the vibration plate 1 is substantially located on at least one of the middle segment 13 and the outer segment 14. Accordingly, the bottom gasket 8 can provide a buffering effect between the vibration plate 1 and the portion of the circuit board 3 having the electrode regions 311a, 311b, 311c by the annular ribs 82, so that the electrode regions 311a, 311b, 311c of the circuit board 3 can receive a larger pressing force.

As shown in FIG. 8 and FIG. 10, the inner gasket 9 in the present embodiment is an annular structure (e.g., an annular rubber) with resilient property. The inner gasket 9 has a hole defined by an inner edge thereof, and a diameter of the hole of the inner gasket 9 is smaller than that of the first hole 11 of the vibration plate 1. The inner gasket 9 includes a main annular body 91 and an abutting annular body 92 slantingly extending from an inner edge of the main annular body 91.

Moreover, the main annular body 91 is disposed on a part of the inner segment 12 of the vibration plate 1 (e.g., an inner part of the inner segment 12 protruding from the circuit board 3 as shown in FIG. 10), and the main annular body 91 is partially arranged in a hole defined by an inner edge of the circuit board 3. The main annular body 91 in the present embodiment is sandwiched between the cup 200a of the container 200 and the vibration plate 1, so that the main annular body 91 can be approximately and gaplessly connected to the cup 200a of the container 200. The abutting annular body 92 is arranged in the first hole 11 of the vibration plate 1, and a free end of the abutting annular body 92 abuts against the microporous member 2.

Figure 14:
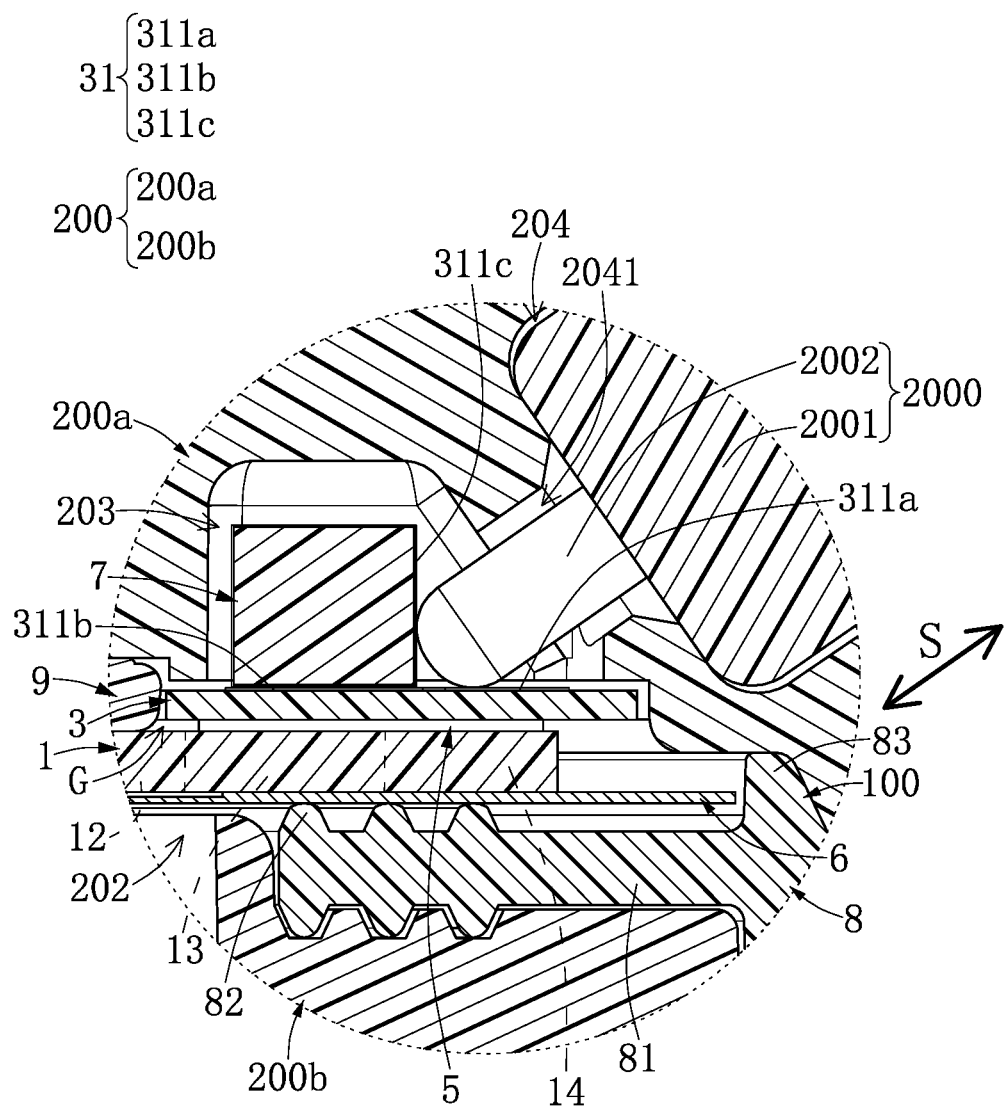
FIG. 14 is an enlarged view of portion XIV of FIG. 2.

As shown in FIG. 3 and FIG. 14, the plug 2000 is detachably inserted into the insertion slot 204 of the container 200 along the insertion direction S, and is electrically coupled to the circuit board 3. The plug 2000 in the present embodiment includes an insulator 2001 and two conductive terminals 2002 each partially embedded in the insulator 2001, and the conductive terminals 2002 are respectively abutted against the two conductive portions 31 of the circuit board 3.

Specifically, each of the conductive terminals 2002 detachably passes through the thru-hole 2041 of the insertion slot 204 and elastically abuts against the two electrode regions 311a, 311c of the corresponding conductive portion 31. Each of the conductive terminals 2002 of the plug 2000 in the present embodiment can simultaneously abut against the corresponding two electrode regions 311a, 311c, thereby increasing the stability of electrical connection between the circuit board 3 and each of the conductive terminals 2002. Moreover, the plug 2000 is electrically coupled to the vibration plate 1 through the circuit board 3 and the solders 4, thereby preventing the vibration of the vibration plate 1 from affecting the stability of electrical connection between the circuit board 3 and the plug 2000.

Figure 15:
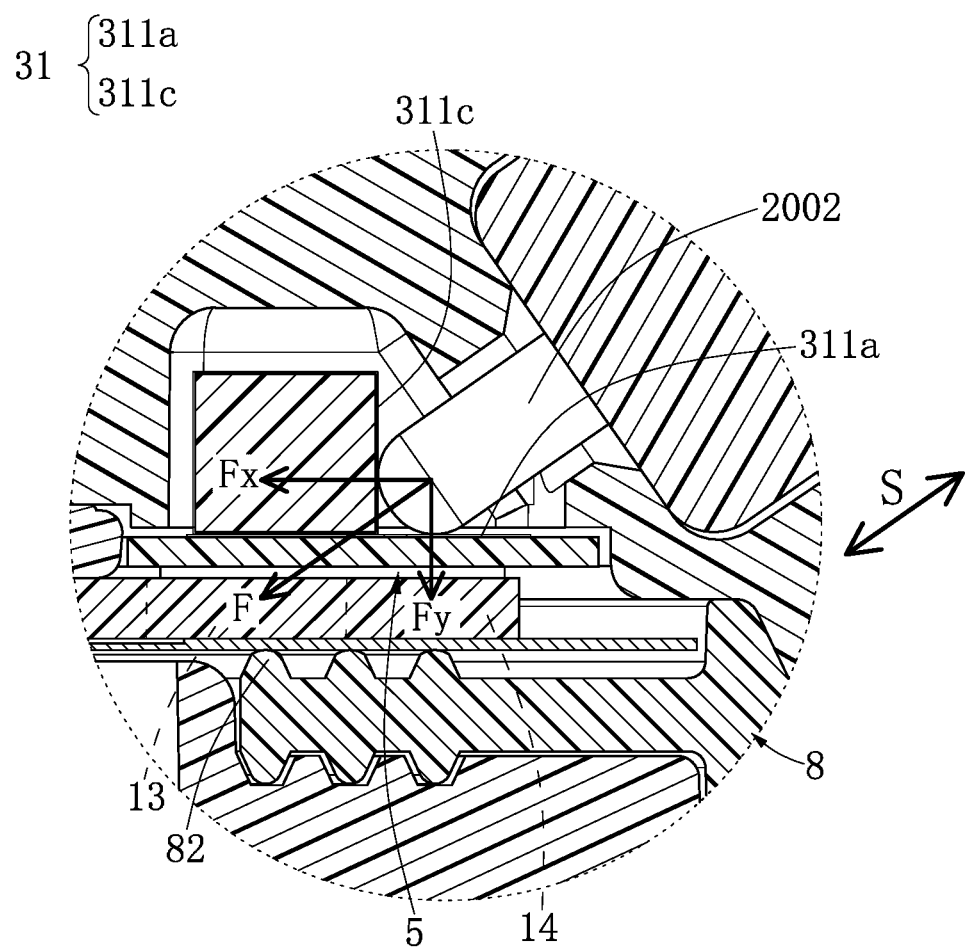
FIG. 15 is a schematic view showing a pressing force from a conductive terminal of FIG. 14.

As shown in FIG. 15, each of the two electrode regions 311a, 311c can receive a pressing force F from the corresponding conductive terminal 2002, and the pressing force F has a horizontal component Fx and a vertical component Fy. Specifically, a portion of each of the two electrode regions 311a, 311c abutted against the conductive terminal 2002 is substantially arranged above at least one of the middle segment 13 and the outer segment 14 of the vibration plate 1, and is substantially arranged above the annular ribs 82 of the bottom gasket 8, so that the buffer 5 and the annular ribs 82 can absorb the vertical component Fy of the pressing force F from the electrode regions 311a (or the terminals 2002).

The number of the conductive terminals 2002 of the plug 2000 in the present embodiment is two, but the present disclosure is not limited thereto. In other embodiments of the present disclosure, the plug 2000 can include only one conductive terminal 2002 that passes through the thru-hole 2041 of the insertion slot 204 and elastically abutted against the corresponding two electrode regions 311a, 311c.

It should be noted that, the aerosol generating device of the present embodiment can be adjusted according to other embodiments of the present disclosure. That is to say, the aerosol generating device provided by the present disclosure can be formed by assembling the features disclosed in the present embodiment and other embodiments.

In conclusion, in the aerosol generator and the atomizing module of the present disclosure, the circuit board is spaced apart from and is electrically coupled to the vibration plate, so that the conductive terminal needs to abut against the circuit board to further be electrically coupled to the vibration plate. Accordingly, the electrical connection between the circuit board and the conductive terminal is not easily affected by the vibration generated from the vibration plate, thereby being more stable.

Moreover, in the aerosol generating device and the aerosol generator of the present disclosure, the atomizing module is provided with the two electrode regions electrically connected to each other and having the same polarity, and the conductive terminal is simultaneously abutted against the two electrode regions to form a multi-point contact, so that the electrical connection between the circuit board (or the vibration plate) and the conductive terminal can be more stable.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An aerosol generator, comprising:
   a container having a liquid chamber and an aerosol chamber; and
   an atomizing module assembled in the container, wherein the liquid chamber and the aerosol chamber are respectively arranged at two opposite sides of the atomizing module, and the atomizing module includes:
      an annular vibration plate having a first hole and including an electrical contact located on a plane;
      a microporous member disposed on the vibration plate and covering the first hole, wherein the liquid chamber and the aerosol chamber are in spatial communication with each other through the microporous member; and a circuit board electrically coupled to the electrical contact and arranged at a side of at least part of the vibration plate, wherein the circuit board and the at least part of the vibration plate have a gap therebetween, and a projected region defined by orthogonally projecting the circuit board onto the plane partially covers the at least part of the vibration plate.

2. The aerosol generator according to claim 1, wherein the atomizing module includes a solder fixed to the electrical contact and the circuit board so as to establish an electrical connection between the electrical contact and the circuit board.

3. The aerosol generator according to claim 2, wherein the vibration plate is sequentially defined as an annular inner segment, an annular middle segment, and an annular outer segment along a direction away from the first hole; a width ratio of the inner segment, the middle segment, and the outer segment in a radius of the vibration plate is 1:3:3; and the electrical contact is arranged on at least one of the middle segment and the outer segment.

4. The aerosol generator according to claim 3, wherein the circuit board includes an external connecting arm arranged directly above at least one of the middle segment and the outer segment, and the solder connects the electrical contact and the external connecting arm.

5. The aerosol generator according to claim 2, wherein the circuit board includes an electrode region and a conductive circuit that is connected to the electrode region, and the electrode region is electrically coupled to the electrical contact through the conductive circuit and the solder.

6. The aerosol generator according to claim 1, wherein the atomizing module includes a buffer sandwiched between the circuit board and a part of the vibration plate, and the gap is arranged between the circuit board and another part of the vibration plate and is in spatial communication with an external space.

7. The aerosol generator according to claim 6, wherein the circuit board includes an electrode region electrically coupled to the electrical contact, and at least part of the buffer is arranged between the electrode region and the vibration plate.

8. The aerosol generator according to claim 1, wherein the atomizing module includes a sheet-like carrier having a second hole, one of the microporous member, the vibration plate, and the carrier is sandwiched between the other two of the microporous member, the vibration plate, and the carrier, and wherein the microporous member covers the second hole, and the liquid chamber and the aerosol chamber are in spatial communication with each other through a portion of the microporous member that covers the second hole.

9. The aerosol generator according to claim 1, wherein the circuit board has a positioning portion fastened to the container so as to hang the circuit board over the at least part of the vibration plate.

10. The aerosol generator according to claim 1, wherein the vibration plate further includes another electrical contact, and the two electrical contacts of the vibration plate are arranged on the same surface of the vibration plate.

11. An atomizing module, comprising:
an annular vibration plate having a first hole and including an electrical contact located on a plane;
a microporous member disposed on the vibration plate and covering the first hole; and
a circuit board electrically coupled to the electrical contact and arranged at a side of at least part of the vibration plate, wherein the circuit board and the at least part of the vibration plate have a gap therebetween, and a projected region defined by orthogonally projecting the circuit board onto the plane partially covers the at least part of the vibration plate.

12. The atomizing module according to claim 11, further comprising a buffer, wherein the buffer is sandwiched between the circuit board and a part of the vibration plate, and the gap is arranged between the circuit board and another part of the vibration plate and is in spatial communication with an external space.

13. The atomizing module according to claim 12, wherein the circuit board includes an electrode region electrically coupled to the electrical contact, and at least part of the buffer is arranged between the electrode region and the vibration plate.

14. The atomizing module according to claim 11, wherein the circuit board includes an electrode region electrically coupled to the electrical contact, and a portion of the projected region with respect to the electrode region is located outside of the electrical contact.

15. The atomizing module according to claim 11, further comprising a solder, wherein the solder is fixed to the electrical contact and the circuit board so as to establish an electrical connection between the electrical contact and the circuit board.

16. The atomizing module according to claim 15, wherein the vibration plate is sequentially defined as an annular inner segment, an annular middle segment, and an annular outer segment along a direction away from the first hole; a width ratio of the inner segment, the middle segment, and the outer segment in to a radius of the vibration plate is 1:3:3; and the electrical contact is arranged on at least one of the middle segment and the outer segment.

17. The atomizing module according to claim 16, wherein the circuit board includes an external connecting arm arranged directly above at least one of the middle segment and the outer segment, and the solder connects the electrical contact and the external connecting arm.

18. The atomizing module according to claim 15, wherein the circuit board includes an electrode region and a conductive circuit that is connected to the electrode region, and the electrode region is electrically coupled to the electrical contact through the conductive circuit and the solder.

19. The atomizing module according to claim 11, further comprising a sheet-like carrier having a second hole, wherein one of the microporous member, the vibration plate, and the carrier is sandwiched between the other two of the microporous member, the vibration plate, and the carrier, and wherein the microporous member covers the second hole.

20. The atomizing module according to claim 11, wherein the vibration plate further includes another electrical contact, and the two electrical contacts of the vibration plate are arranged on the same surface of the vibration plate.

* * * * *